June 2, 1964 J B. WILLIAMS Plant Pat. 2,409
ROSE PLANT
Filed Jan. 10, 1963
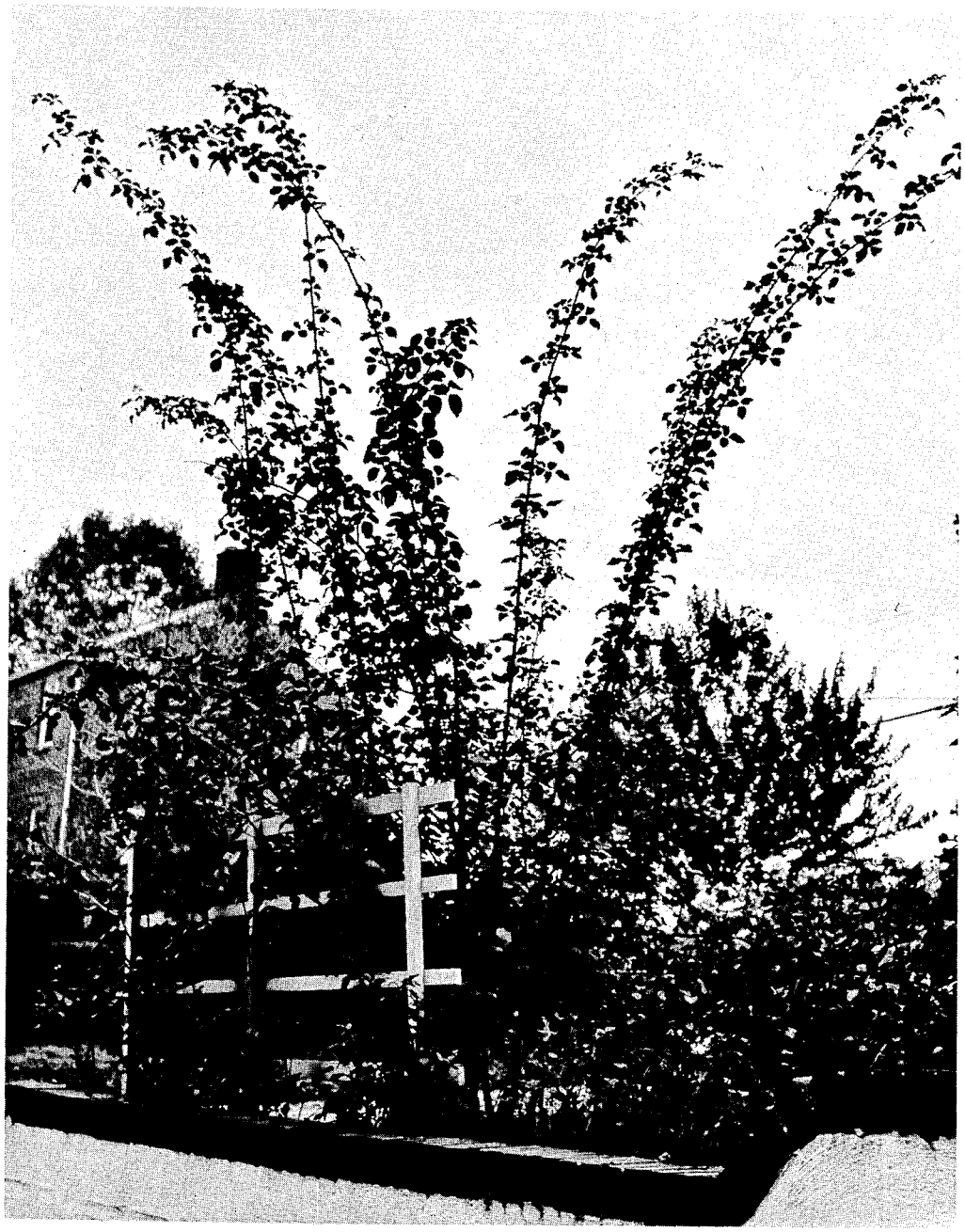

United States Patent Office

Plant Pat. 2,409
Patented June 2, 1964

2,409
ROSE PLANT

J Benjamin Williams, 2800 Elnora St., Silver Spring, Md.

Filed Jan. 10, 1963, Ser. No. 250,724
1 Claim. (Cl. Plt.—3)

The present invention relates to a new and distinct variety of rose plant of the climbing floribunda class, which originated as a sport of the variety, "Ivory Fashion" (Plant Patent No. 1,688).

The new variety was discovered by me at my residence in Silver Spring, Maryland, in a cultivated area. My attention was drawn to a plant that was presumed to be the variety, Ivory Fashion, but which exhibited definite climbing characteristics in that it produced canes which were 8 to 10 feet in length. This new variety has been asexually reproduced by budding, under my supervision, at West Grove, Pennsylvania. Observations of the above asexual reproductions of the new variety have shown that the climbing habit comes true to form and is transmissible through succeeding asexual propagations.

In view of the fact that the new variety is distinguished from its parent only by its climbing habit of growth, it is unnecessary to describe the new variety in detail, since it conforms substantially to the detailed description appearing in Plant Patent No. 1,688, dated March 11, 1958, to which reference may be readily had.

The accompanying drawing shows a specimen plant of the new variety which is illustrative of the typical climbing habit of growth.

I claim:

A new and distinct variety of rose plant of the climbing floribunda class, substantially as herein shown and described, characterized particularly as to novelty by its general similarity to its parent variety, Ivory Fashion (Plant Patent No. 1,688), but differing therefrom by its pronounced climbing growth habit.

No references cited.